United States Patent [19]

Adams et al.

[11] Patent Number: 5,092,902

[45] Date of Patent: Mar. 3, 1992

[54] HYDRAULIC CONTROL UNIT FOR PROSTHETIC LEG

[75] Inventors: Thomas C. Adams; Lanny K. Wiggins, both of Centerville, Ohio

[73] Assignee: Mauch Laboratories, Inc., Dayton, Ohio

[21] Appl. No.: 743,583

[22] Filed: Aug. 9, 1991

Related U.S. Application Data

[63] Continuation of Ser. No. 568,241, Aug. 16, 1990.

[51] Int. Cl.⁵ .......................... A61F 2/64; A61F 2/74
[52] U.S. Cl. ..................................... 623/26; 623/44; 92/84; 92/110
[58] Field of Search ........................ 623/39, 43, 44, 26; 92/85 B, 85 R, 84, 110, 112

[56] References Cited

U.S. PATENT DOCUMENTS

| | | | |
|---|---|---|---|
| 2,859,451 | 11/1958 | Mauch | 623/39 |
| 3,316,558 | 5/1967 | Mortensen. | |
| 4,065,815 | 1/1978 | Sen-Jung. | |
| 4,212,087 | 7/1980 | Mortensen. | |
| 4,578,082 | 3/1986 | Sen-Jung. | |
| 4,595,179 | 6/1986 | Glabiszewski. | |
| 4,662,486 | 5/1987 | Stenberg | 623/39 X |
| 4,880,213 | 11/1989 | Shinbori et al. | 92/48 X |

FOREIGN PATENT DOCUMENTS

| | | | |
|---|---|---|---|
| 1074522 | 2/1984 | U.S.S.R. | 623/44 |
| 1428371 | 10/1988 | U.S.S.R. | 623/39 |

Primary Examiner—Randall L. Green
Assistant Examiner—David H. Willse
Attorney, Agent, or Firm—Jacox & Meckstroth

[57] ABSTRACT

A prosthetic leg has a pivotal knee joint and a hydraulic fluid control unit connected to provide variable forces which dampen flexion and extension of the knee and also bias the leg to its extended position. The unit includes an aluminum housing lined with an axially adjustable sleeve and control bushing defining a cylindrical chamber which receives a piston mounted on a tubular piston rod. The housing and chamber receive hydraulic fluid or oil which flows during movement of the piston through fluid control ports, channel and adjustable gaps defined by the sleeve and bushing for damping the movement of the rod. The piston rod encloses a gas filled flexible bladder which forms an oil accumulator during inward movement of the piston rod and also produces variable forces for moving the piston rod outwardly to its extended position. The housing confines a gap defining ring which compensates for changes in oil viscosity with heat.

12 Claims, 1 Drawing Sheet

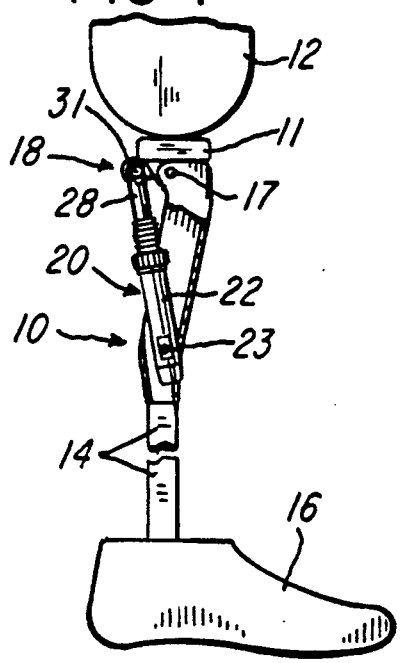
FIG-1
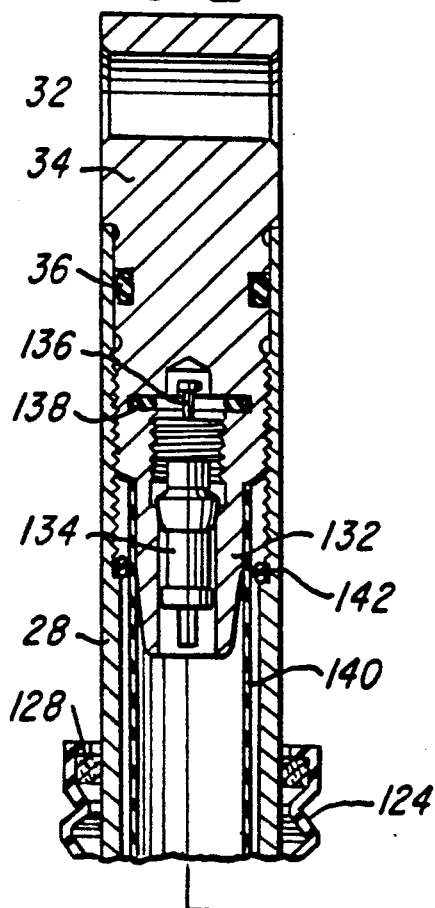
FIG-2
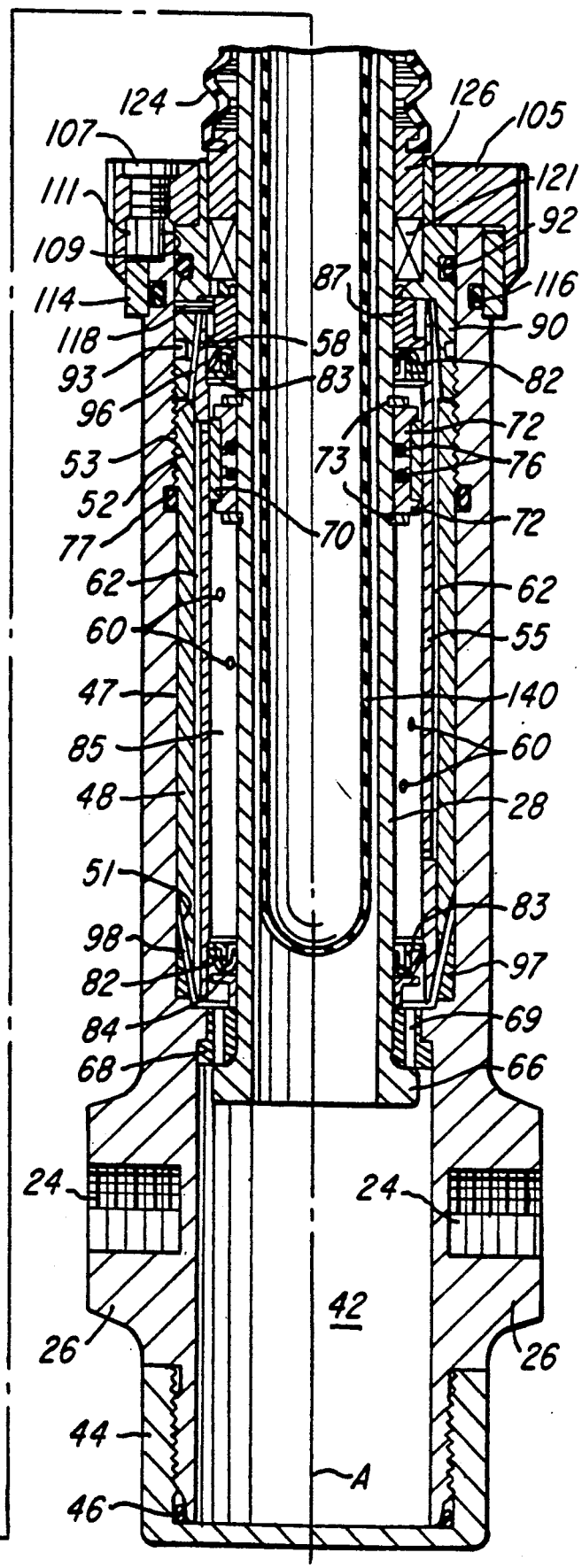

HYDRAULIC CONTROL UNIT FOR PROSTHETIC LEG

This is a continuation of application Ser. No. 568,241, filed Aug. 16, 1990.

BACKGROUND OF THE INVENTION

In the art of hydraulic fluid control cylinders or units for use in a prosthetic leg at the knee joint, for example, as disclosed in U.S. Pat. No. 2,859,451 assigned to the Assignee of the present invention, it is desirable to minimize the size and weight of the unit while providing variable and adjustable damping forces or moments during flexion and extension of the knee and also variable biasing forces for moving the leg to its extended position. As disclosed in the above mentioned U.S. Pat. No. 2,859,451, the hydraulic control unit generally includes a housing which defines an oil reservoir, and a cylinder projects downwardly into the housing in spaced relation. The cylinder confines a control bushing which defines a staggered array of ports connected by corresponding axially extending channels to tapered passages or gaps at opposite ends of the bushing for controlling the oil flow when a piston and piston rod move axially within the bushing to produce variable damping forces. The bushing is axially adjustable within the cylinder for independently adjusting the tapered gaps according to the constant damping forces desired.

A hydraulic fluid control unit of the type disclosed in U.S. Pat. No. 2,859,451 has also been constructed by Applicants' Assignee with a coil compression spring located within the housing and surrounding the cylinder for engaging an annular seal and piston confined between the cylinder and housing. This spring and annular piston form an oil accumulator which receives the displaced hydraulic fluid when the piston rod is forced into the cylinder and housing. The spring biased annular piston also produce an increasing biasing force against the oil as the knee flexes and functions to urge the piston rod outwardly for returning the artificial leg to its extended or generally straight position. Other forms of hydraulic fluid control units for prosthetic legs are disclosed in U.S. Pat. Nos. 3,316,558, 4,065,815, 4,212,087, 4,578,082 and 4,595,179.

SUMMARY OF THE INVENTION

The present invention is directed to an improved hydraulic control unit for use with a knee joint of a prosthetic leg and which also produces variable forces to produce movement of the prosthetic leg simulating that of the natural leg over a wide range walking speeds. The control unit of the invention provides the desirable features and advantages of reduced size and weight, convenient adjustment of the variable biasing force applied to extend the prosthetic leg as well as convenient adjustment of the damping forces applied during flexion and extension of the knee. In addition, the control unit of the invention has fewer parts, is more economical in construction and more dependable in operation.

The above advantages are provided in a preferred embodiment of the invention wherein an aluminum tubular housing defines a hydraulic fluid or oil reservoir and holes for receiving pivot pins. The housing is lined with a cylindrical sleeve which tightly surrounds and cooperates with a cylindrical control bushing to define a staggered array of hydraulic control ports and axially extending channels or passages through which the oil flows to produce variable damping forces. A tubular piston rod extends into the housing through the control bushing and supports a piston for sliding contact with the bushing Annular one way check valves are supported within opposite end portions of the bushing adjacent tapered annular flow control gaps, and the bushing and sleeve are adjustable axially within the housing for independently adjusting the gaps to select the desired constant damping forces which resist knee flexion and extension.

The tubular piston rod encloses an elongated flexible rubber-like bladder which is filled with a pressurized gas through a valve within the outer end portion of the rod. The gas pressurized bladder cooperates with the tubular piston rod to form an oil accumulator as the piston rod moves into the housing and progressively increases the pressure on the oil and piston rod as the angle of knee flexion increases. The bladder pressurized oil produces an upward biasing force on the piston rod to urge the leg to its extended position, and the pressure on the oil also forces oil into the control bushing to replace any oil that is lost over an ID extended period of use.

Other features and advantages of the invention will be apparent from the following description, the accompanying drawing and the appended claims.

BRIEF DESCRIPTION OF THE DRAWING

FIG. 1 is an elevational view of a prosthetic leg with a portion broken away to show the assembly of a hydraulic control unit constructed in accordance with the invention; and FIG. 2 is an axial section of the hydraulic control unit shown in FIG. 1 and enlarged about twice its normal size for showing detail construction of the unit.

DESCRIPTION OF THE PREFERRED EMBODIMENT

FIG. 1 illustrates a prosthetic or artificial leg 10 which includes a bracket 11 secured to a cup-shaped socket portion 12 adapted to receive the thigh portion of an amputee's leg. The prosthetic leg 10 also includes a hollow lower leg portion 14 which projects upwardly from a foot portion 16 and is pivotally connected to the bracket 11 by a hinge pin 17 to form a knee joint 18. In accordance with the present invention, a hydraulic control unit 20 extends between the bracket 11 and the lower leg portion 14 and includes a machined aluminum cylinder or housing 22 which has an axis A and is pivotally connected to the lower leg portion 14 by a pair pivot pins 23 extending from the leg portion 14 into corresponding threaded bores 24 (FIG. 2) formed within outwardly projecting bosses 26 of the housing 22. The unit 20 also includes a tubular chrome plated steel piston rod 28 which projects from the housing 22 and is connected to the bracket 11 by a pivot pin 31. The pin 31 extends through a cross bore 32 (FIG. 2) formed within an aluminum fitting 34 threaded into the outer end portion of the piston rod 28 and confining a resilient O-ring 36 to form a fluid-tight seal between the fitting 34 and outer end portion of the piston rod 28.

Referring to FIG. 2, the lower end portion of the housing 22 defines a cylindrical hydraulic fluid or oil reservoir 42 which is closed by a bottom cap 44 threaded onto the lower end portion of the housing 22 and sealed to the housing by a resilient O-ring 46. The upper end portion of the housing 22 defines a cylindrical bore 47 which receives a cylindrical brass liner or sleeve 48 having a tapered or frusto-conical lower end surface 51 and an externally threaded upper end portion 52 which engages internal threads 53 formed within the upper end portion of the housing 22. The sleeve 48 is press-fitted with a brass liner or control bushing 55 which has a tapered frusto-conical lower end surface mating with the surface 51 and a tapered or frusto-conical upper end surface 58.

The control bushing 55 also has a staggered array of axially and circumferentially spaced flow control passages or ports 60 which extend through the bushing into corresponding circumferentially spaced and axially extending channels or passages 62 formed within the outer surface of the bushing. As a result of the tight fit of the control bushing 55 within the sleeve 48, each channel 62 forms an oil flow control passage which extends from a port 60 to either the lower tapered end surface 51 of the sleeve 48 or the upper tapered end surface 58 of the control bushing 55.

The tubular piston rod 28 has an inner end portion which projects into the housing 22 and includes a flange 66 forming the inner end of the piston rod. The flange 66 normally engages a guide bearing 68 having a set of four circumferentially spaced and axially extending oil flow passages 69. The bushing 68 guides the inner end portion of the piston rod 28 when the piston rod moves axially into the housing 22 and also limits the outward movement of the piston rod to its extended position shown in FIGS. 1 and 2.

The piston rod 28 carries a cylindrical steel piston 70 which is retained by a pair of annular collars 72 located on the piston rod 28 by a pair of retaining rings 73. A pair of resilient O-rings 76 form fluid-tight seals between the collars 72 and the piston rod 28, and a larger resilient O-ring 77 restrains rotation of the sleeve 48. An annular rubber-like flexible valve element 82 is retained within a counterbore formed within the lower end portion of the control bushing 55 between a ring 83 and a ring 84 seated on the bearing 68. The element 82 forms a one way check valve which permits oil to flow only upwardly into an annular chamber 85 defined between the outer surface of the piston rod 28 and the inner surface of the control bushing 55.

Another annular valve element 82 and ring 83 are retained in a counterbore formed within the upper end portion of the bushing 55 and form a one way check valve which permits oil to flow only downwardly into the chamber 85. The upper annular valve element 82 is retained within the counterbore by an annular collar 87 having an upper portion swagged or secured to an annular cover screw 90 having a lower end portion threaded into the housing 22 directly above the threaded upper end portion of the sleeve 48. The cover screw 90 is rotatable within the upper end portion of the housing 22, and a resilient O-ring 92 forms a fluid-tight seal between the screw 90 and housing 221 and restrains rotation of the screw 90. A groove 93 forms a thread relief on the screw. A tapered or frusto-conical internal surface is formed within the annular cover screw 90 and opposes the mating tapered surface 58 on the upper end portion of the bushing 55 to form therebetween an upper annular tapered flow passage or gap 96. An annular titanium sleeve 97 is seated within the lower end of the bore 47 and has an inner tapered or frusto-conical surface which cooperates with the opposing and mating tapered surface 51 to define a lower flow passage or gap 98. The upper gap 96 is adjustable by rotating the cover screw 90 with a surrounding cap 105 which is secured to the cover screw. A limit pin 107 is threaded into the cap 105 and projects into a notch or recess 109 which extends circumferentially approximately 330° around the end upper end portion of the housing 22 to limit rotation of the cap 105 and cover screw 90. The limit pin 107 also projects into a recess 111 which extends circumferentially approximately 180° within the upper end portion of an indicating ring 114 mounted for rotation on the upper end portion of the housing 22. A resilient O-ring 116 holds the indicating ring 114 on the housing 22 after the ring 114 is set.

A radial pin 118 projects from the cover screw 90 through a notch or recess extending circumferentially approximately 180° within the upper end portion of the control bushing 55. The inner end portion of the pin 118 is received within an annular recess formed within the outer portion of the ring or collar 87. Thus rotation of the cover screw 90 by the cap 105 is effective to rotate the assembly of the sleeve 48 and control bushing 55 and adjust the assembly axially within the bore 47 to adjust the bottom tapered gap 98. The upper tapered gap 96 is then adjusted by rotation of the cover screw 90 with the cap 105 relative to the assembly of the sleeve and control bushing.

The cover screw 90 also retains an annular oil seal 121 which slidably engages the outer surface of the piston rod 28, and the exposed surface portion of the piston rod which engages the seal 121 is protected by a bellows-type collapsible tube or casing 124. The lower end portion of the protective casing 124 is retained by an annular ring 126 pressed into the upper end portion of the cover screw 90 above the rod seal 121, and the upper end portion of the protective casing is positively secured to a felt ring 128 which slides on the piston rod 28.

The upper internally threaded end portion of the piston rod 28 encloses a tubular fitting 132 which receives a Schrader-type valve 134 having a spring biased depressible valve stem 136. A resilient O-ring 138 forms a fluid-tight seal between the fitting 34 and the fitting 132. The fitting 132 projects into the upper end portion of an elongated rubber-like flexible bladder 140 which extends into the tubular piston rod 28 and has a closed lower end. The bladder 140 is bonded by adhesive to the fitting 132, and a resilient O-ring 142 forms a fluid-tight seal between the upper end portion of the bladder 140 and the piston rod 28. The bladder 140 is inflated through the valve 134 with a pressurized gas such as nitrogen.

After the entire hydraulic control unit 20 is assembled, and the reservoir 42 and chamber 85 are filled with a predetermined volume of hydraulic fluid such as oil, the bladder 140 is inflated with a gas supplied through the Schrader valve 134 before the fitting 34 is assembled. The gas is pressurized so that a predetermined pressure is exerted on the oil within the reservoir chamber 42 and the lower end portion of the piston rod 28. The pressurized oil exerts a force outwardly on the piston rod 28 to bias the rod to its normally extended position as shown in FIGS. 1 and 2 when the leg 10 is in its extended position. This variable biasing force exerted by the oil may be conveniently adjusted simply by changing the pressure of the gas within the bladder 140.

The hydraulic control unit 20 is installed within a prosthetic leg so that it spans the knee joint and the piston rod 28 is pushed into the housing 22 whenever the knee flexes or pivots on the cross pin 17. As the piston rod 28 moves inwardly, the rod is subjected to a changing hydraulic resistance or damping force by the piston 70 forcing oil outwardly through the control ports 60 located below the piston 70 and through the channels or passages 62. The oil displaced within reservoir 42 by the piston rod 28 is forced upwardly into the piston rod 28 compressing and partially collapsing the bladder 140 so that the piston rod 28 and bladder 140 function as a pressurized oil accumulator. As the pressure of the gas within the bladder 140 increases with further flexing of the knee, the biasing force exerted by the oil against the piston rod 28 increases so that a greater biasing force is exerted on the lower leg portion 14 for moving it towards its extended position shown in FIG. 1.

As the piston 70 moves downwardly within the chamber 85, the oil forced outwardly from the chamber 85 through the ports 60 is forced upwardly within the corresponding channels 62, through the upper tapered restriction gap 96 and downwardly past the upper one way annular check valve 82 into the chamber 85 above the piston 70. At the beginning of the compression stroke, all of the ports 60 and channels 62 serve as restricting fluid passages. However, as the piston 70 moves downwardly over the staggered holes or ports 60 in the control bushing 55, the number of ports 60 decreases thereby producing a higher resistance to oil flow and knee flexion as the angle of knee flexion increases. This is important for preventing excessive heal rise of the foot 16 throughout a wide range of walking speeds.

During extension of the piston rod 28 and the prosthetic leg 10, the process is reversed, and oil above the piston 70 within the chamber 85 flows outwardly through the control passages or ports 60 located above the piston 70, downwardly through the channels 62 which open into the lower tapered gap 98 and then back upwardly through the lower check valve 82 and into the chamber 85 below the piston 70. As in knee flexion, the number of control ports and channels 62 available for oil flow decreases as the piston moves upwardly and approaches the end of its motion or stroke. This upward movement of the piston to increasingly higher resistance is important in order to decelerate the leg movement and prevent an abrupt stop of the leg as it reaches its extended limit when the piston rod 28 is fully extended.

In addition to the damping force profile created by the staggered arrangement of the control ports 60, a constant damping force is created by restricting the oil flow through the upper and lower gaps 96 and 98, respectively. As mentioned above, the gaps are adjustable by turning the cap 105 which, in turn, adjusts the cover screw 90 and the control bushing axially 55 and sleeve 48 within the housing 22. This allows for independent adjustment of the upper and lower gaps and the resistance to knee flexion or extension, permitting each user to select the ideal set of resistances for his or her unique biomechanical needs.

From the drawing and the above description, it is apparent that a prosthetic leg having a knee joint equipped with a hydraulic control unit constructed in accordance with the invention, provides desirable features and advantages. For example, the construction of the hydraulic control unit 20 with the oil accumulator within the piston rod 28 provides for significantly reducing the size and weight of the unit, eliminates noise of operation and eliminates parts which wear. The unit 20 also provides for conveniently adjusting the pressure exerted by the hydraulic fluid or oil simply by adjusting the pressure of the gas within the bladder 140. In addition, the unit provides for conveniently adjusting the constant damping forces by independently adjusting the upper gap 96 and the lower gap 98. The construction of the control unit 20 also provides for greater reliability, simplifies construction and manufacturing, allows for greater part tolerances which provides for reducing the cost of the components assembled to form the unit 20. Also, the passages 69 within the bearing 68 and the pressure exerted on the oil by the bladder 140 assures that the upper portion of the unit is always full of oil even if a little oil seeps by the rod seal 121 after an extended period of use. Preferably, the flexible wall of the bladder 140 is always slightly collapsed so that there is no pressure loss across the bladder wall due to the elasticity of the bladder resisting stretching of the bladder. It has also been found that by using dissimilar materials across each of the gaps 96 and 98, such as the titanium sleeve 98 and the brass sleeve 48 in control bushing 55, the lower gap 98 narrows slightly as the temperature of the unit 20 increases after continuous use of the leg 10, thereby offering some compensation for the reduced oil viscosity with the higher temperature. This permits the use of the lower weight or aluminum housing 22 in order to reduce weight and machining costs.

While the form of control unit 20 or apparatus herein described constitutes a preferred embodiment of the invention, it is to be understood that the invention is not limited to this precise form of apparatus, and that changes may be made therein without departing from the scope and spirit of the invention as defined in the appended claims.

The invention having thus been described, the following is claimed:

1. An improved hydraulic control unit for use with a knee joint of a prosthetic leg for producing movement of the prosthetic leg simulating that of the natural leg over a wide range of walking speeds, said unit comprising an elongated tubular housing having an axis, said housing including a lower end portion defining a reservoir and continuing axially with an upper end portion defining a bore, a sleeve lining said bore and slidably supported by said upper end portion for axially adjustable movement, a control bushing disposed within said sleeve and defining a chamber for receiving a hydraulic fluid, said bushing and sleeve having means defining a series of flow control passages extending through said bushing from said chamber and axially between said bushing and said sleeve, a tubular piston rod having an inner portion extending into said chamber and an outer portion projecting from said housing, a piston on said inner portion of said piston rod and slidably engaging said bushing, a supply of hydraulic fluid within said reservoir and said chamber, said fluid flowing through said passages in response to axial movement of said piston and said piston rod within said chamber to effect damping of said piston rod, said tubular piston rod defining a chamber having an inner end open to said reservoir and providing for the free unrestricted flow of said fluid between said reservoir and said chamber within said piston rod, an extendable and compressible member within said chamber in said tubular piston rod, and said extendable and compressible member providing for resiliently biasing the free flow of fluid into said piston rod chamber from said reservoir in response to fluid displacement by inward movement of said piston rod into said reservoir.

2. A control unit as defined in claim 1 and including means within said outer portion of said piston rod for precisely adjusting said biasing force exerted by said extendable and compressible member within said piston rod according to the personal preferences of the individuals using the prosthetic leg.

3. A control unit as defined in claim 1 wherein said extendable and compressible member within said piston rod comprises a flexible rubber-like bladder, and a check valve within said outer portion of said piston rod for introducing and confining a volume of pressurized gas within said bladder for selecting said biasing force exerted against said hydraulic fluid and piston rod.

4. A control unit as defined in claim 3 and including a fitting threaded axially into said outer portion of said piston rod, and said valve includes a spring biased valve member supported within said fitting.

5. A control unit as defined in claim 1 wherein said upper end portion of said housing has internal threads, said sleeve has external threads engaging said internal threads, and means mounted on said housing for rotating said sleeve to provide axial adjustment of said sleeve.

6. A control unit as defined in claim 1 wherein said control bushing has a frusto-conical lower end surface, a ring member disposed within said bore of said housing and having an internal frusto-conical inner surface surrounding said lower end surface to define a gap therebetween, and said control bushing and ring member are formed of different materials to control said gap in response to heating of said unit and a lower viscosity of said fluid.

7. A control unit as defined in claim 1 wherein said housing retains an annular bearing having a bore slidably supporting said inner portion of said piston rod, and said bearing having at least one passage for directing fluid in an axial direction through said bearing.

8. An improved hydraulic control unit for use with a knee joint of a prosthetic leg for producing movement of the prosthetic leg simulating that of the natural leg over a wide range of walking speeds, said unit comprising an elongated tubular housing having an axis, said housing including a lower end portion defining a reservoir and continually axially with an upper end portion defining a bore, a sleeve lining said bore and slidably supported by said upper end portion for axially adjustable movement, a control bushing disposed within said sleeve and defining a chamber for receiving a hydraulic fluid, said bushing and sleeve having means defining a series of flow control passages extending through said bushing from said chamber and axially between said bushing and said sleeve, a tubular piston rod having an inner portion extending into said chamber and an outer portion projecting from said housing, a piston on said inner portion of said piston rod and slidably engaging said bushing, a supply of hydraulic fluid within said reservoir and said chamber, said fluid flowing through said passages in response to axial movement of said piston and said piston rod within said chamber to effect damping of said piston rod, said tubular piston rod defining a chamber having an inner end open to said reservoir and providing for the free unrestricted flow of said fluid between said reservoir and said chamber within said piston rod, a gas filled extendable and compressible bladder within said chamber in said tubular piston rod, a fitting threaded into said outer portion of piston rod and supporting a spring biased valve for adjusting the pressure of the gas within said bladder, and said bladder providing for resiliently biasing the free flow of hydraulic fluid into said piston rod chamber from said reservoir in response to fluid displacement by inward movement of said piston rod into said reservoir.

9. A control unit as defined in claim 8 wherein said housing includes said upper portion having internal threads, said sleeve has external threads engaging said internal threads, and means mounted on said housing for rotating said sleeve to provide axial adjustment of said sleeve.

10. A control unit as defined in claim 8 wherein said control bushing has a frusto-conical lower end surface, a ring member mounted within said bore of said housing and having an internal frusto-conical inner surface surrounding said lower end surface to define a gap therebetween, and said control bushing and ring member are formed of different materials to control said gap in response to heating of said unit and a lower viscosity of said fluid.

11. A control unit as defined in claim 10 wherein said housing is formed of a substantially lighter weight material than the material forming said ring member.

12. A control unit as defined in claim 8 wherein said housing retains an annular bearing having a bore slidably supporting said inner portion of said piston rod, and said bearing having at least one passage for directing fluid in an axial direction through said bearing.

* * * * *